(12) United States Patent
Joseph (10) Patent No.: US 12,082,844 B2
(45) Date of Patent: Sep. 10, 2024

(54) MULTIPURPOSE VAGINAL OCCLUSION AND DISTENSION DEVICE WITH DISTENSION CONTROLLER

(71) Applicant: Lalu Joseph, Kerala (IN)

(72) Inventor: Lalu Joseph, Kerala (IN)

( * ) Notice: Subject to any disclaimer, the term of this patent is extended or adjusted under 35 U.S.C. 154(b) by 86 days.

(21) Appl. No.: 15/733,356

(22) PCT Filed: Jun. 11, 2018

(86) PCT No.: PCT/IN2018/000033
§ 371 (c)(1),
(2) Date: Jul. 9, 2020

(87) PCT Pub. No.: WO2019/202605
PCT Pub. Date: Oct. 24, 2019

(65) Prior Publication Data
US 2021/0022770 A1      Jan. 28, 2021

(30) Foreign Application Priority Data

Apr. 18, 2018   (IN) .............................. 201841014797

(51) Int. Cl.
*A61B 17/42*     (2006.01)
*A61B 17/00*     (2006.01)
(Continued)

(52) U.S. Cl.
CPC .......... *A61B 17/42* (2013.01); *A61B 17/1204* (2013.01); *A61B 17/12099* (2013.01);
(Continued)

(58) Field of Classification Search
CPC ................ A61B 17/42; A61B 17/1204; A61B 17/12099; A61B 17/12136; A61B 2017/00805; A61F 5/4553; A61F 6/08
See application file for complete search history.

(56) References Cited

U.S. PATENT DOCUMENTS

7,591,830 B2 *   9/2009   Rutter ................. A61M 25/104
                                                                  128/207.15
9,055,973 B2 *   6/2015   Varma .................. A61B 17/442
(Continued)

*Primary Examiner* — Tan-Uyen T Ho
*Assistant Examiner* — David P Stein
(74) *Attorney, Agent, or Firm* — ASLAN LAW, P.C.

(57) ABSTRACT

The invention relates to a Multipurpose Vaginal Occlusion and Distension Device with Distension Controller, which helps patients with Female Stress Urinary Incontinence and for Fecal Incontinence. It comprises of double layered cylindrical body (101) making inflatable annular space and with closed anterior (103) and posterior (104) wall provided with inflatable tubular silicon ribs (103*a*, 104*a*), but the posterior end is provided with gas flow tube (106) connectable to the "Distension control and release mechanism" by which the cylindrical cavity (107), annular space, tubular ribs at both the end can be inflated. But the same device can be used, if the anterior end (301) is opened for collecting menstrual blood during Menstrual Cycle as an alternative to menstrual cups and pads. The same can be used preferably with partly opened mouth (403) by Doctors during Laparoscopic Surgeries as a pneumoseal and as a vaginal blocker to prevent the gas leakage through the vaginal canal while performing the colpotomy and thereafter during vaginal vault suturing.

3 Claims, 4 Drawing Sheets

(51) Int. Cl.
*A61B 17/12* (2006.01)
*A61F 5/455* (2006.01)
*A61F 6/08* (2006.01)
(52) U.S. Cl.
CPC ...... *A61B 17/12136* (2013.01); *A61F 5/4553* (2013.01); *A61F 6/08* (2013.01); *A61B 2017/00805* (2013.01)

(56) References Cited

U.S. PATENT DOCUMENTS

| | | | | |
|---|---|---|---|---|
| 2010/0312204 A1* | 12/2010 | Sheu | ............... | A61F 5/4408 604/330 |
| 2013/0138135 A1* | 5/2013 | Rosen | ............... | A61B 17/12 606/197 |
| 2016/0287259 A1* | 10/2016 | Hanson | ............ | A61B 17/12109 |
| 2018/0014829 A1* | 1/2018 | Tal | ................ | A61B 17/12145 |
| 2018/0280059 A1* | 10/2018 | O'Brien, III | ............ | A61K 35/19 |
| 2021/0059856 A1* | 3/2021 | Eshel | ............... | A61M 25/1002 |

* cited by examiner

MULTIPURPOSE VAGINAL OCCLUSION AND DISTENSION DEVICE WITH DISTENSION CONTROLLER

FIELD OF INVENTION

This invention generally relates to a Multipurpose Vaginal Occlusion and Distension Device with Distension Controller, which helps patients with Female Stress Urinary Incontinence and for Fecal Incontinence. But according to another embodiment under the invention, the same device can be used as Reinforced Multipurpose Vaginal Occlusion and Distension Device with Distension Controller for collecting menstrual blood during Menstrual Cycle as an alternative to menstrual cups and pads as well as for Doctors during Laparoscopic Surgeries as a pneumoseal and as a vaginal blocker to prevent the gas leakage through the vaginal canal while performing the colpotomy and thereafter during vaginal vault suturing, without applying any manual pressure using cotton gauze or plastic vaginal tubes which are currently used during hysterectomies and similar surgeries.

The Multipurpose Vaginal Occlusion and Distension Device with its novel cylindrical construction according to the instant invention will not allow the device to slip off from its position once placed inside the vaginal canal and it will give uniform distension throughout the vaginal canal as the distention of the device can be controlled by the Distension Control and Release Mechanism which is part of the device. The Distension Control and Release Mechanism is either inbuilt or detachable and can be connected as and when needed.

BACKGROUND OF THE INVENTION

Studies have shown that one out of five female above the age group of 30 suffer from Stress Urinary Incontinence. This uncontrollable menace brings huge embarrassment to women, most women prefer non surgical correction for this disease and the present options available are vaginal cones and vaginal weights which are to be inserted inside the vaginal canal, and also may be used for the purpose of progressive resistive pelvic floor muscular exercise. However, there is little scientific evidence to suggest that vaginal weight training is superior to pelvic floor muscle exercise in women with stress urinary incontinence. The difficulties in routinely doing pelvic floor exercise and its inconsistent result and the issues of Vaginal Cones and vaginal weights falling off from the vaginal cavity, and the feel of having extra weight inside the vagina are some of the major drawbacks of such devices. To obviate these drawbacks, I have developed the new Multipurpose Vaginal Occlusion and Distension Device with Distension Control and Release Mechanism primarily for female Stress Urinary Incontinence. The same device can also be used by ladies for replacing the Menstrual Cups and Pads often used during menstrual period, as well as by the Surgeons during laparoscopic gynecology surgeries as a pneumoseal and vaginal blocker with slight modification without deviating from the novel inventive features of the invention explained above.

No doubt there are a number of prior art patents/applications available in the related areas and some of them are mentioned hereby way of reference.

U.S. Pat. No. 7,763,033 B2 discloses a systems, methods, apparatus and devices for performing improved gynecologic and urologic procedures. Patient benefit is achieved through improved outcomes, reduced pain, especially peri-procedural pain, and reduced recovery times. The various embodiments enable procedures to be performed outside the hospital setting, such as in a doctor's office or clinic. Distension is achieved mechanically, rather than with liquid distension media, thereby limiting the risk of intravasation.

US 2004/0153097 A1 relates to treatment for post partum hemorrhage which discloses an intravaginal clamping device for occluding a female patient's uterine artery. The device comprising of: a.) an first clamping means which has an elongated handle with a distal operative end and a proximal manipulative end and a clamping element Secured to the operative distal end at an obtuse angle with respect to the first handle; b). a Second clamping means which has a Second elongated handle with a distal operative end and a proximal manipulative end and a Second clamping element Secured to the operative distal end of the Second elongated handle at an obtuse angle with respect to the Second elongated handle; and c). a pivotal connecting means between the first and Second clamping means So that rotation of the first and Second handles about the pivotal connection adjusts spacing between the first and Second clamping elements.

US20100087798A1 relates to systems, methods, apparatus and devices for performing improved gynecologic and urologic procedures using a flowable distension media. The system and devices provide simplified use and reduced risk of adverse events. Patient benefit is achieved through improved outcomes, reduced pain, especially peri-procedural pain, and reduced recovery times.

The various embodiments enable procedures to be performed outside the hospital setting, such as in a doctor's office or clinic.

US20080245371A1 discloses a systems, methods, apparatus and devices for performing improved gynecologic and urologic procedures are disclosed. The system and devices provide simplified use and reduced risk of adverse events. Patient benefit is achieved through improved outcomes, reduced pain, especially peri-procedural pain, and reduced recovery times. The various embodiments enable procedures to be performed outside the hospital setting, such as in a doctor's office or clinic.

US20050107818A1 relates to a Vaginal delineation and occlusion device. A vaginal delineator, capable of adjusting to varying lengths of the cervix and angles of the fornix is disclosed. A diaphragm for occluding the vagina, preventing leakage of carbon dioxide from the peritoneal cavity is attachable to the delineator. In an additional embodiment, the vaginal delineator comprises a cup to which a ring is pivotally attached. In this embodiment, the cup acts as the occlusion device.

US20060015144A1 relates to uterine artery occlusion staple. The invention is directed to an intravaginal staple for occluding a female patient's uterine artery in the treatment of a uterine disorder such as fibroids, DUB, PPH, uterine bleeding after caesarian delivery and the like. The intravaginal staple includes an occluding bar having a pressure applying surface and at least one and preferably two tissue penetrating legs which are provided with protuberances which help to retain the staple leg within the penetrated tissue. At least part of the staple is preferably formed of bio absorbable material so that it will in part self destruct at a preselected time period by separation of staple components caused by the bio absorption of a bio absorbable portion of the staple. The staple deployment system may be provided with elongated handles and staple deploying mechanisms on the distal ends of the handles to drive the legs of the staple into the tissue bundle about the uterine artery so that pressure applied by the occlusion bar occludes the uterine artery.

US20080245371A1 relates to Systems, methods and devices for performing gynecological procedures. The system and devices provide simplified use and reduced risk of adverse events. Patient benefit is achieved through improved outcomes, reduced pain, especially peri-procedural pain, and reduced recovery times. The various embodiments enable procedures to be performed outside the hospital setting, such as in a doctor's office or clinic.

US20100180422A1 relates to a Vaginal delineating device. A gynecological instrument for delineating the fornix of the vagina during laparoscopic surgeries having a spring, which proximal end is affixed to a solid ring and the distal end is affixed to a base. The extension of the base can be inserted into the head of the Valtchev® Uterine Mobilizer and locked in place. The solid ring can be tilted in any direction, and can come closer to the base, allowing automatic adjustment for the angles of the fornix of the vagina and the cervical length.

US20100312204A1 relates to a menstrual cup device and a method of us thereof includes a menstrual cup made of expandable material so as to be compressed, the menstrual cup having resilience for restoring to its original shape after being compressed, the menstrual cup comprising a pulling stem at a lower end thereof, a circular lip at an open upper end thereof, and a circular groove below the circular lip; and a collection bag having a resilient restraining ring at an open upper end thereof; thereby, the resilient restraining ring being expanded to be constricted in the circular groove of the menstrual cup, the circular lip being adapted to prevent the resilient restraining ring from disengagement, the menstrual cup with the collection bag being compressed and inserted into the vagina for collecting menstrual blood, the collection bag being disposable and replaceable.

Given the above, it's a big challenge to come out with a multipurpose holistic solution by designing a Reinforced and Modified Multipurpose Vaginal Occlusion and Distension Device with Distension Controller which can be used for 1) female stress urinary incontinence and fecal incontinence. 2) collecting menstrual blood during menstrual cycle, alternative to menstrual cups and menstrual pads and 3) for laparoscopic gynecological surgeries as a vaginal blocker and pneumoseal.

OBJECTS OF THE INVENTION

The main objective of the invention is to provide a squeezable and inflatable cylindrical device which can be used for Female Stress Urinary incontinence and fecal Incontinence, Another objective of the invention is to provide inflatable tubular ribs at the edges of the cylindrical device or spiral ribs wound around the body of the cylindrical Multipurpose Vaginal Occlusion and Distension Device so that the device can be made tightly fit in the vaginal canal as per need.

Yet another objective of the invention is to provide inflatable annular space formed by the double layer wall of the cylindrical device and by inflating the annular space it can provide soft cushioning effect while placed inside the vaginal canal.

One more objective of the invention is to provide both anterior and posterior wall of the Multipurpose Vaginal Occlusion and Distension Device closed but with an air inflow inlet connected outside at the posterior wall to facilitate inflating the device when used for Stress Urinary Incontinence and fecal incontinence.

Still another objective of the invention is to provide corrugated or smooth flexible outer wall of the Multipurpose Vaginal Occlusion and Distension Device for desired fit inside the vaginal canal.

Another objective of the invention is to provide the detachable Distension Control and Release Mechanism connected to the gas inflow inlet at the outer posterior wall of the device.

Yet another objective of the invention is to provide the Distension Control and Release Mechanism with an air inflow inlet, air pumping chamber (bellows), flexible tube having multiple channels to inflate the annular space, the tubular ribs and also the internal cavity of the device and with the gas releasing and locking valve and an adapter port connect to the gas inflow tube at the posterior wall of the device.

One more objective of the invention is to provide the Multipurpose Vaginal Occlusion and Distension Device with a fully circular mouth opening at the anterior portion to make the device usable for menstrual bleeding.

Yet another objective of the invention is to provide the Multipurpose Vaginal Occlusion and Distension Device with a corrugated or inflatable spiral tubular ribbed or smooth outer wall to make it comfortably fit inside the vaginal canal as per choice of the user.

One more objective of the invention is to provide the Multipurpose Vaginal Occlusion and Distension Device with a sensor chip embedded at the blood level marker at the internal space of the device which will be around 5 mm below the mouth opening such that it gives an alarm warning by an application which can be programmed with the users wristwatch or mobile phone, In the event if the device is filled more than the desired level, Another objective of the invention is to provide the gas inlet extended to the level of the sensor chip at the upper blood level marker of the device, wherein the blood will not be flowing out through the inflating or deflating tube while used as a menstrual device Another objective of the invention is to provide the Multipurpose Vaginal Occlusion and Distension Device with sensor chips embedded at the internal wall of the device to sense and measure the quantity of blood collected during every usage of the device by an alarm warning with an application which can be programmed and linked to the user's wristwatch or mobile phones Yet another objective of the invention is to provide the Multipurpose Vaginal Occlusion and Distension Device with slight modification to make it usable during Laparoscopic gynecological surgeries as a pneumoseal and a vaginal blocker with single or double layer construction.

One another objective of the invention is to provide said Multipurpose Vaginal Occlusion and Distension Device with partly opened or with small multiple circular openings at the anterior wall to enable the device to get filled up with $CO_2$ from the abdominal cavity and also to provide structural support to the pelvic floor during laparoscopic surgery.

Yet another objective of the invention is to provide the Multipurpose Vaginal Occlusion and Distension Device having the anterior wall opened and with a closed posterior wall with an inbuilt tubular retractor means to pull out the device after the usage in laparoscopic surgeries.

Another objective of the invention is to provide the Multipurpose Vaginal Occlusion and Distension Device with optional gas inlet as in case the distension is insufficient by the CO2 from abdominal cavity during laparoscopic surgeries.

Yet another objective of the invention is to provide the Multipurpose Vaginal Occlusion and Distension Device reversible inside out and outside in and used such that it can give different strength of fitment inside the vaginal canal depending on the need of the procedure.

SUMMARY OF THE INVENTION

The Multipurpose Vaginal Occlusion and Distension Device with Distension Controller, according to the invention, is primarily used for controlling Female Stress Urinary Incontinence and for Fecal Incontinence as an alternative to vaginal cones and vaginal weights.

According to another embodiment under the invention, the same device with minor alteration can be used for collecting menstrual blood during Menstrual Cycle as an alternative to vaginal/menstrual cups and pads.

According to yet another embodiment under the invention, it can be adapted by doctors during Laparoscopic Surgeries as a pneumoseal to prevent gas leakage and as vaginal blocker with minor modification of the device.

The main part of the Multipurpose Vaginal Occlusion and Distension Device is a cylindrical vessel of different sizes which are of 1 cm to 8 cm diameter and of 2 cm to 8 cm length, made of single or two layered flexible polymeric membrane having a thickness of 0.5 to 4. mm forming the wall of the cylindrical part. The outer layer of the cylindrical body of the device is made of corrugated or smooth flexible polymeric membrane. The anterior side is open while the posterior side is closed with the same material when it is used for collecting menstrual blood and is an alternative to menstrual cups and pads hitherto used.

The anterior side of the said cylindrical vessel which is open is having silicon rib at the edge formed by semi flexible metallic ring engulfed inside the silicon rib which is inflatable. Similarly, at the posterior side of the said cylindrical vessel which is closed is also provided with silicon rib at the edge formed by semi flexible metallic ring engulfed inside the silicon rib which is inflatable. The inflating is done externally by connecting to "Distension control and release mechanism" and filling the gas/air by bellows provided therein. But in the case of Stress urinary incontinence and fecal incontinence both anterior and posterior walls are closed but with a gas inflow inlet is provided at the posterior wall.

According to another embodiment under the invention, the cylindrical part can be reinforced by a tubular spiral rib which is Inflatable tubular rib made of silicon with or without metallic spring thread engulfed by silicon, which is wound spirally over the cylindrical part and is connectable to the tubular silicon rim at the inlet side as well as at the bottom of the cylindrical part.

According to another embodiment under the invention, squeezable and inflatable Multipurpose Vaginal Occlusion and Distension Device with a full mouth opening or partly opened circular mouth or with circular multiple openings on the anterior wall with a closed posterior wall having a flexible silicon thread functioning as retractor means for removing the device from vaginal cavity is disclosed.

According to a preferred embodiment under the invention, the posterior wall can have gas inflow inlet tube with provision for opening and closing which can be connected to "Distension control and release mechanism".

Any of these devices based on the requirement, the surgeon can squeeze and insert into the vaginal cavity. Doctors during Laparoscopic Surgeries use this device as a pneumoseal to prevent gas leakage and as vaginal blocker during colpotomy and thereafter for vaginal vault suturing.

Normally in laparoscopic surgeries the CO2 gas already filled up available inside the abdomen will help to fill up the device while doing the colpotomy and if needed the device can also be filled up externally as per another embodiment.

DETAILS OF THE DRAWINGS

These objectives and other features, aspects, and advantages of the present invention will be better understood when the detailed description is read with reference to the following drawings according to a preferred embodiment under the invention.

FIG. 4.1: Multipurpose Vaginal Occlusion and Distension Device with fully open mouth with provision to attach Detachable "Distension control and release mechanism at the posterior end of the cylindrical space that is suitable for during Laparoscopic Surgeries, according to an embodiment under the invention FIG. 4.2: Multipurpose Vaginal Occlusion and Distension Device with partly opened mouth with provision to attach Detachable "Distension control and release mechanism at the posterior end of the cylindrical space that is suitable for during Laparoscopic Surgeries, according to another embodiment under the invention.

FIG. 4.3: Multipurpose Vaginal Occlusion and Distension Device for having mouth with multiple opening with provision to attach Detachable "Distension control and release mechanism at the posterior end of the cylindrical space, that is suitable for during Laparoscopic Surgeries, according to yet another embodiment under the invention.

FIG. 4.1a: Multipurpose Vaginal Occlusion and Distension Device for Laparoscopic Surgeries, with fully opened mouth while the posterior end is closed and provided with flexible silicon thread that is suitable for during Laparoscopic Surgeries, according to an embodiment under the invention.

FIG. 4.2a: Multipurpose Vaginal Occlusion and Distension Device with partly opened mouth while the posterior end is closed and provided with flexible silicon thread that is suitable for during Laparoscopic Surgeries, according to another embodiment under the invention.

FIG. 4.3a: Multipurpose Vaginal Occlusion and Distension Device having mouth with multiple opening while the posterior end is closed and provided with flexible silicon thread that is suitable for during Laparoscopic Surgeries, according to yet another embodiment under the invention.

Wherein the Parts of the Multipurpose Vaginal Occlusion and Distension Device and Figure indicators are named below:
101—Cylindrical body made of double layered polymeric membrane; 102—Double layer polymeric membrane of the cylindrical body; 102a—Corrugated outer layer of the cylindrical body; 103—Anterior wall of the cylindrical body; 103a—Inflatable tubular rib at the anterior edge of the cylindrical body; 104—Posterior wall of the cylindrical body; 104a—Posterior tubular rib at the posterior edge of the cylindrical body; 105—Inflatable tubular rib spirally wound around the cylindrical body; 106—Gas flow pipe fixed at the tubular opening at the posterior end of the cylinder; 107—Cavity of the cylindrical body of the device; 201—Connector port of the "Distension control and release mechanism"; 202—Gas pumping bellows chamber of the "Distension control and release mechanism"; 203—Gas inflow and outflow tube of the "Distension control and release mechanism"; 204—Gas inlet/out valve having multiple channel of the "Distension control and release mechanism"; 205—Coupling port with gas releasing and locking valve that can be connected to the "Distension control and release mechanism"; 301—Circular mouth of the fully opened cylindrical body; 302—Smooth outer layer of the cylindrical body; 303—Corrugated outer layer of the cylindrical body; 304—Extended gas inflow inlet tube inserted inside the cylindrical cavity of the device; 305—Cylindrical body opened at the anterior end; 306,306a,306b, and 306c— Sensor chip embedded at the Blood level marker inside the cylindrical body of the device; 307—Blood level marker inside the cylindrical body of the device; 401—Fully opened mouth of the cylindrical body; 402—Partly opened mouth of the cylindrical body; 403—Mouth with multiple opening of the cylindrical body; 404—Flexible silicon thread functioning as retractor means; 405—Gas flow tube connected with Coupling port (205) with gas releasing and locking valve that can be connected to the "Distension control and release mechanism" so that it functions as retractor means, once the "Distension control and release mechanism" is detached; 501—Vaginal canal; 601—The circular rib at the anterior part of the traditional vaginal/Menstrual cup as per prior art; 602—The conical body of the vaginal cup/Menstrual cup as per prior art;

DETAILED DESCRIPTION OF THE INVENTION

Features of the present invention will become apparent to those skilled in the art upon reading the following detailed description of the instant invention.

The Multipurpose Vaginal Occlusion and Distension Device according to the instant invention, will be an important device for patients as an alternative as an easy to use and effective device where the new Multipurpose Vaginal Occlusion and Distension Device helps to control the stress urinary incontinence easily. Being light weight, adjustable distention and pressure control mechanism and controlled release and fit in the vaginal canal, the ease to inflate and deflate the device using the Distension Control and Release Mechanism and uniform pressure applied throughout the sphincter muscle helps the patients in better control of Stress Urinary Incontinence. Apart from stress urinary incontinence, the multi ribbed and structurally tensioned device helps in supporting Fecal Incontinence.

Menstrual cups and pads are often used during menstrual period. The need to frequently change the pads, disposal issues and also the drawback of the present menstrual cups which fall off from the vagina where it is placed due to the conical shape of such devices make it important for ladies of their menstrual age to use the innovative Multipurpose Vaginal Occlusion and Distension Device with Distension Control and Release Mechanism for collecting menstrual blood during menstrual cycle. The squeezable double layered cylindrical device with its circular mouth which will get snuggly fit to the vaginal walls, with reinforced and inflatable tubular ribs and annular space to keep the device inflated and to keep comfortably inside the vaginal canal and the closed posterior wall of the device with gas inflow inlet connected to the Distension Control and Release Mechanism makes it convenient to women for easy and safe use of the Multipurpose Vaginal Occlusion and Distension Device which will not be slipped off from vagina canal and can be taken out as and when needed using the Distension Control and Release Mechanism and also the device is available in different diameter and length and with varying features.

Laparoscopic procedures require the abdominal cavity to be filled with gas, forming pneumoperitoneum to allow the surgeon to see and move instruments and perform procedure inside the abdominal cavity. During laparoscopic gynecology surgeries, since using the vaginal canal as a route for extraction of the abdominal tissues masses after colpotomy, the gas tends to escape through the vaginal opening, making it difficult to maintain the vision for the doctors, during the laparoscopic surgical procedures. In addition, the size of women's vaginal canal varies considerably and that demands the use of the new Multipurpose Vaginal Occlusion and Distension Device as it can block the gas leakage and also give enough and controlled distension to the vaginal canal uniformly using the Distension Control and Release Mechanism of the device. The squeezable and inflatable device with its cylindrical construction, tubular ribs make it snuggly fit inside the vaginal canal so that it will not be slipped off. The opening at the anterior wall of the device makes the device to get filled with CO2, such that the device will work as pnuemoseal and the closed posterior wall of the device having a tubular retractor means allow the device to be taken out after usage.

Figures 1, 1A:
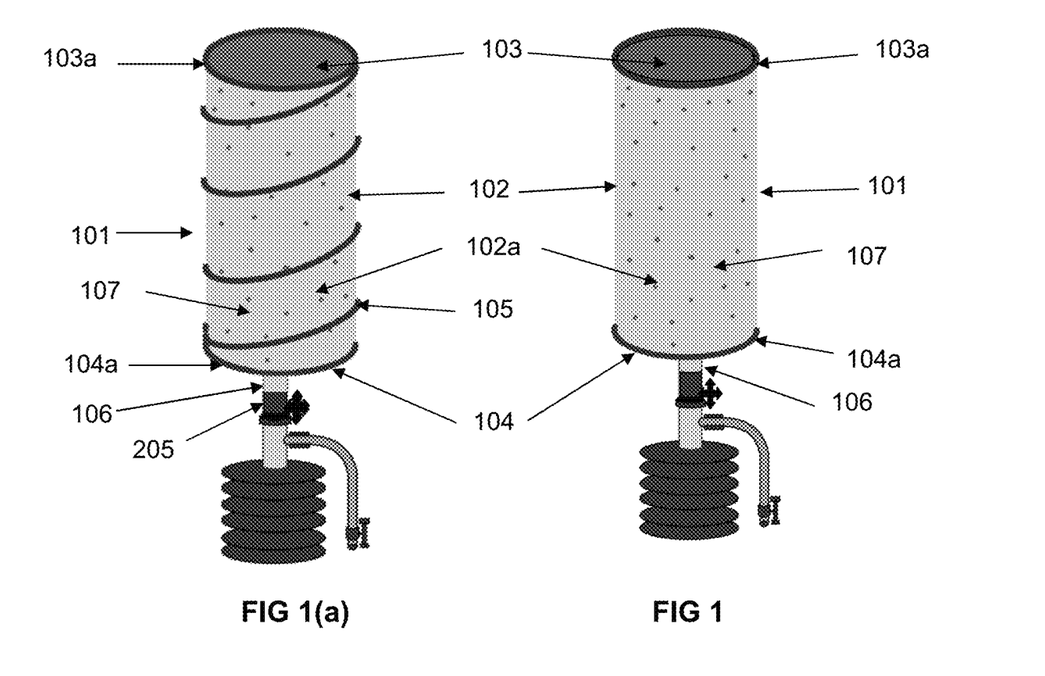
FIG. 1: Multipurpose Vaginal Occlusion and Distension Device having the corrugated outer layer according to the invention.
FIG. 1a: Multipurpose Vaginal Occlusion and Distension Device having the corrugated outer layer with inflatable tubular spirally wound around the cylinder which can be used for Stress Urinary Incontinence and for Fecal Incontinence, according to yet another embodiment under the invention

The "Multipurpose Vaginal Occlusion and Distension Device for Stress Urinary Incontinence and for Fecal Incontinence" is a squeezable and inflatable device is shown in FIG. 1 and FIG. 1a. As shown in FIG. 1, it can be single layered or double layered, preferably double layered (102) cylindrical construction (101) made of flexible polymeric material, having a thickness of 0.5 to 4. mm with different diameter and length with anterior (103) end and posterior (104) ends closed. The outer layer of the cylindrical body of the device is made of corrugated or smooth flexible polymeric membrane. An annular space is formed in between the two layers is inflatable. Similarly cylindrical hollow internal space also can be inflated. The posterior end is provided with a tubular opening having gas flow pipe (106). The anterior end of the said cylindrical body (101) is having silicon rib (103a) at the edge formed by semi flexible metallic ring engulfed inside the silicon rib which is inflatable. Similarly, at the posterior end of the said cylindrical vessel is having silicon rib (104a) at the edge formed by semi flexible metallic ring engulfed inside the silicon rib which is inflatable.

In a preferred embodiment under the invention, as shown in FIG. 1a, the cylindrical body (101) can be reinforced by a tubular spiral rib (105) which is Inflatable made of silicon with or without metallic soft spring thread is engulfed by silicon, which is wound spirally over the cylindrical part and is connectable to the tubular silicon rim at the inlet side as well as at the posterior of the cylindrical part.

Figure 2:
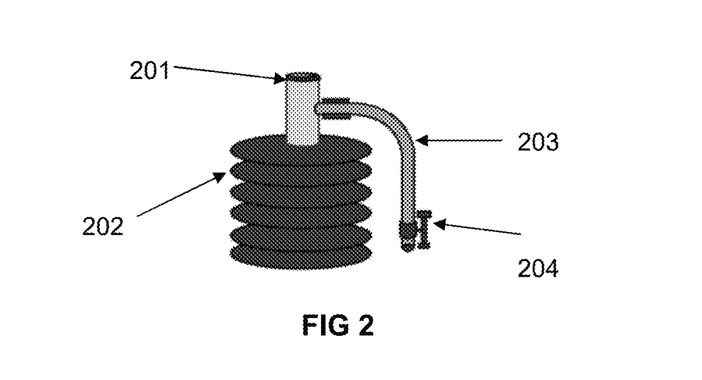
FIG. 2: "Distension control and release mechanism" of the Multipurpose Vaginal Occlusion and Distension Device, according to a preferred embodiment under the invention.

FIG. 2 shows the "Distension control and release mechanism" of the Multipurpose Vaginal Occlusion and Distension Device wherein the connector port (201) of the device can be connected to the air inflow inlet (106) at the posterior wall of the Multipurpose Vaginal Occlusion and Distension Device by means of a Coupling port (205) with gas releasing and locking valve. The out let of the air pumping bellows chamber (202) is also connected to the gas inflow and outflow tube (203) having multiple channel to inflate the flexible annular space, flexible tubular rib, both at the anterior end (103) as well as posterior end (104), in addition to a tubular spiral rib (105) wound around the cylindrical surface and inflatable cylindrical hollow internal space built with a closed anterior wall. The gas inlet/out valve (204) provided on the gas inflow and outflow tube (203) will act as gas releasing valve as well as the gas locking valve.

According to another embodiment under the invention, the "Multipurpose Vaginal Occlusion and Distension Device for Stress Urinary Incontinence and for Fecal Incontinence" can be modified so as to use the same for collecting menstrual blood during Menstrual Cycle as an alternative to vaginal/menstrual cups and pads with a detachable "Distension control and release mechanism.

Figure 3:
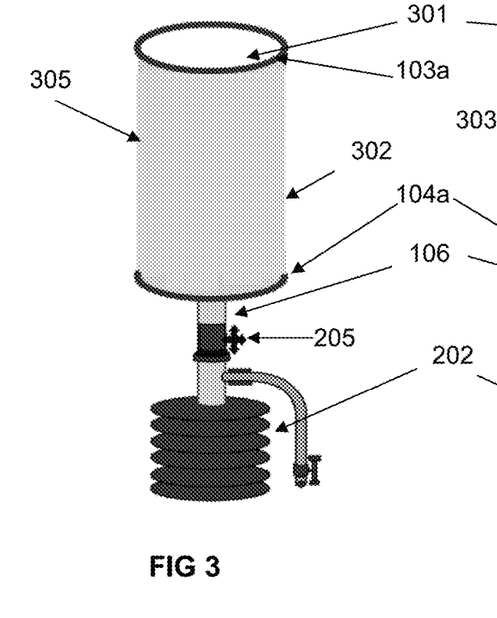
FIG. 3: Modified version of the Multipurpose Vaginal Occlusion and Distension Device attached with "Distension control and release mechanism" with single smooth layer on the cylindrical wall which can be used for collecting Menstrual Blood, according to an embodiment under the invention.

As shown in FIG. 3 the Multipurpose vaginal occlusion and distension device the cylindrical body (101) is having dia ranging from 1 cm to 8 cm and length ranging from 2 cm to 8 cm, is made of a single layer polymeric membrane with smooth outer layer (302) having a thickness of 0.5 to 4. mm with fully opened the anterior end (301) and closed posterior end provided with a tubular opening reinforced with tubular rib (103a), (104a) respectively formed by semi flexible metallic ring engulfed inside the silicon rib which are inflatable along with flexible annular space formed at the cylindrical wall. The, posterior end is provided with a tubular opening having gas flow tube (106) which is connected to the connector port (201) of said "Distension control and release mechanism" by means of Coupling port (205) with gas releasing and locking valve and the out let of the air pumping bellows chamber (202) is connected to the gas inflow and outflow tube (203) provided with gas inlet/out valve (204) and wherein the cylindrical body is insertable in the vaginal cavity for holding menstrual blood during menstrual period.

Figure 3A:
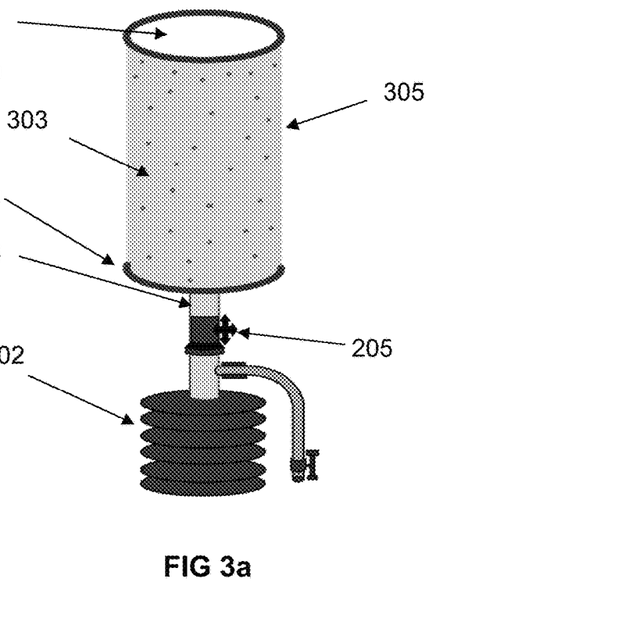
FIG. 3a: Multipurpose Vaginal Occlusion and Distension Device attached with "Distension control and release mechanism" having double layered layer out of which the outer layer is corrugated one, which can be used for collecting Menstrual Blood, according to another embodiment under the invention.

FIG. 3a shows the Multipurpose vaginal occlusion and distension device attached with "Distension control and release mechanism" similar to the one shown in FIG. 3, but it is a double walled cylindrical vessel and the outer layer of the cylindrical body (305) is corrugated (303) so that it helps to make it comfortably fit inside the vaginal canal once the cylindrical body is inserted inside the vaginal canal. for collecting the menstrual blood.

Figure 3B:
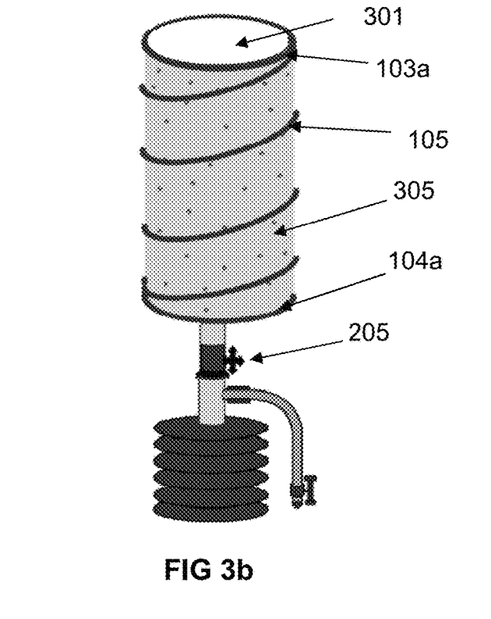
FIG. 3b: Multipurpose Vaginal Occlusion and Distension Device attached with "Distension control and release mechanism" having the corrugated outer layer with inflatable tubular rib spirally wound around the cylinder, which can be used for collecting Menstrual Blood, according to another embodiment under the invention.

FIG. 3b shows the Multipurpose Vaginal Occlusion and Distension Device attached with "Distension control and release mechanism" the cylindrical body (305) with open anterior end is reinforced by a tubular spiral rib (105) wound around the cylindrical body which is inflatable made of silicon with or without metallic soft spring engulfed by silicon, and connected to the tubular silicon rib of the mouth and posterior end respectively, so that air pumping bellows (202) of the "Distension control and release mechanism" simultaneously inflating inflatable tubular rib at the anterior edge (103a) of the cylindrical body, inflatable tubular rib at the posterior edge (104a); inflatable tubular rib (105) spirally wound around the cylindrical body (305); and the annular space formed in between the wall of the cylinder wall. Here the inflatable tubular rib (105) spirally wound around the cylindrical body helps to make it comfortably fit inside the vaginal canal once the cylindrical body is inserted inside the vaginal canal for collecting the menstrual blood.

According to FIG. 3c, which is a Transparent view of multipurpose Vaginal Occlusion and Distension Device attached with "Distension control and release mechanism" the gas inflow inlet (304) is extended inside the cylindrical cavity of the device the height of which will be 0.5 cm below the mouth opening (301) and the sensor chip (306,306a, 306b, and 306c) is embedded at the blood level marker (307) at the internal space of the device for collecting Menstrual Blood. The gas inflow inlet is made to extended (304) inside the cavity of the device such that the menstrual blood will not come out through the gas tube and the sensor chip (306, 306a, 306b, and 306c) embedded at the blood level marker (307) at the internal space of the device, such a way that it gives an alarm warning based on the desired blood level indicator setting by an application which can be programmed and can be used by with the user's wristwatch or mobile phone. In the event if the device is filled more than the desired level, and also the censer chips embedded at different level inside the device, based on the setting, sense and measure the quantity of blood collected during every usage of the device.

Once the cylindrical part of the device is inserted inside the vaginal cavity and coupling port with gas releasing and locking valve (205) provided on the extended gas inflow inlet tube (106) protruding outside the cylinder requires to be closed, the detachable "Distension control and release mechanism is detached and is deployed only when the mensural blood is required to be emptied.

Figure 4:
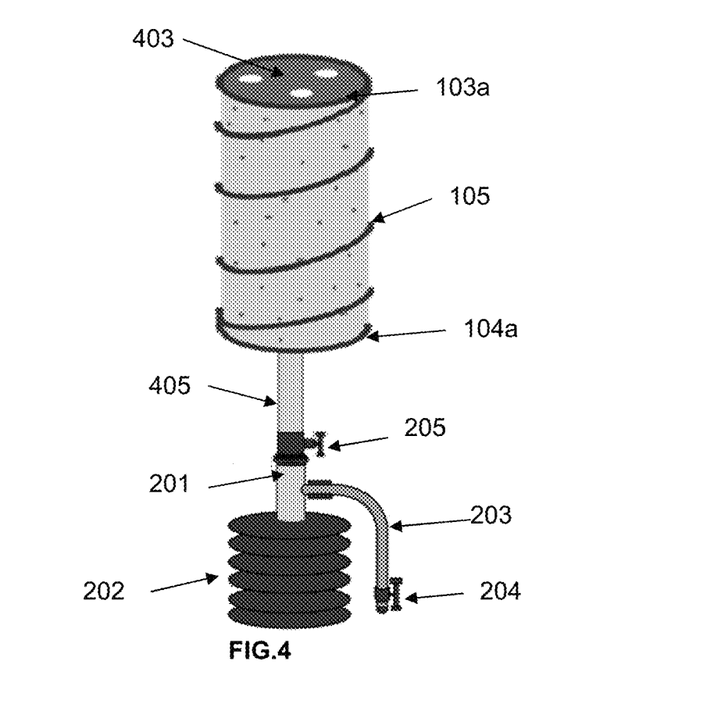
FIG. 4: Multipurpose Vaginal Occlusion and Distension having mouth with multiple opening with inflatable tubular spirally wound around the cylinder, and attached with "Distension control and release mechanism" that is suitable for during Laparoscopic Surgeries, according to an embodiment under the invention.

According to another embodiment under the invention, the Multipurpose vaginal occlusion and distension device can be made use by Doctors during Laparoscopic Surgeries as a pneumoseal and as a vaginal blocker to prevent the gas leakage through the vaginal canal while performing the colpotomy and thereafter during vaginal vault suturing, without applying any manual pressure using cotton gauze or plastic vaginal tubes which are currently used during hysterectomies and similar surgeries. The cylindrical body having dia ranges from 1 cm to 8 cm and length ranging from 2 cm to 8 cm, is made single or double layer polymeric membrane having a thickness of 0.5 to 4. mm and the anterior end is fully opened (401) or partially opened (402) or having multiple circular opening (403) as shown in FIG. 4.1, FIG. 4.2 and FIG. 4.3 respectively. As shown in FIG. 4, the circular cylindrical mouth as well as the posterior end are reinforced with tubular rib (103*a*), (104*a*) respectively formed by semi flexible metallic ring engulfed inside the silicon rib which are inflatable along with flexible annular space formed at the cylindrical wall, in the case of double layered wall. In another embodiment under the invention inflatable tubular spiral ribs (105) can be wound around the cylindrical body rough the body. The posterior wall is provided with a tubular opening having gas flow tube (405) and is connected to the connector port (201) of the "Distension control and release mechanism" having the gas pumping bellows chamber (202) by means of a Coupling port (205) with gas releasing and locking valve, and the outlet of the air pumping bellows chamber (202) is connected to the gas inflow and outflow tube (203) provided with gas inlet/out valve (204), so that it is insert able in the vaginal cavity before colpotomy, so that abdominal cavity which is filled with gas, forming pneumoperitoneum to allow the laparoscopic surgeon to see and move instruments and perform procedure especially vaginal vault suturing inside the abdominal cavity without any gas loss.

The "Distension control and release mechanism" can be used to inflate not only the cavity (107) of the cylindrical body, but also the flexible annular space formed by the double layered polymeric membrane (102), flexible tubular rib at the anterior circular edge (103*a*), posterior circular edge (104*a*), tubular rib spirally wound (105) around the cylindrical body as shown in FIG. 4.

Figures 42, 43:
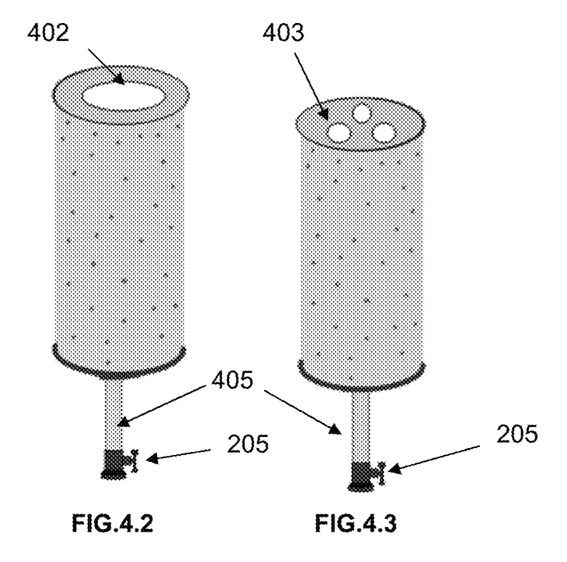

During the laparoscopic surgery, the $CO_2$ gas will get filled in the device through the fully opened mouth (401), partly opened mouth (402) or mouth with multiple opening (403) of the cylindrical body depending on the usage of the type the device having different type of cylindrical body used during colpotomy and vaginal vault suturing. The cylindrical cavity of the device can also be filled up even using the distension control and release mechanism connected through gas pipe line provided at the posterior end of the device and or with an external gas connection, if the device is not getting properly filled up during colpotomy and vaginal vault suturing with the $CO_2$ filled up the abdominal cavity. However, the unopened portion of anterior wall of the device as shown in FIG. 4.2 and FIG. 4.3 give structural pressure support to the pelvic floor.

This gas inflow inlet can be connected the "Distension control and release mechanism" helps to give additional distention to the device in case, the distension from the abdominal cavity is insufficient. Said "Distension control and release mechanism" can be removed after filling the cylindrical cavity of the device with adequate quantity of $CO_2$, if it was necessitated during colpotomy and vaginal vault suturing.

According to another embodiment under the invention, Multipurpose Vaginal Occlusion and Distension Device as shown in FIG. 4.1*a*, FIG. 4.2*a* and FIG. 4.3*a* can also be used for Laparoscopic Surgeries. Here the anterior wall of the device is fully opened in the case of FIG. 4.1*a*; partly opened in the case of FIG. 4.2*a* and having multiple opening as shown in FIG. 4.3*a*, while the posterior wall of the device is fully closed and provided with flexible silicon thread (404) functioning as retractor means to pull out the device after usage instead of gas inflow inlet tube (405) fitted with coupling port with gas releasing and locking valve (205) that can be connected to the "Distension control and release mechanism"

Figure 5:
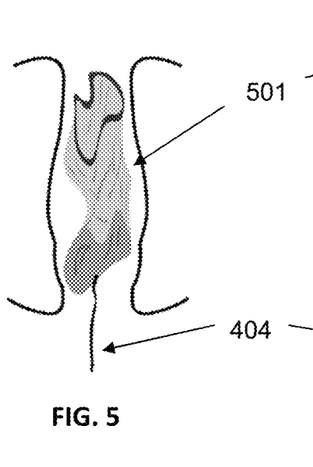
FIG. 5: Multipurpose Vaginal Occlusion and Distension Device inserted into the vaginal canal after squeezing the device, according to yet another embodiment under the invention.
Figure 5A:
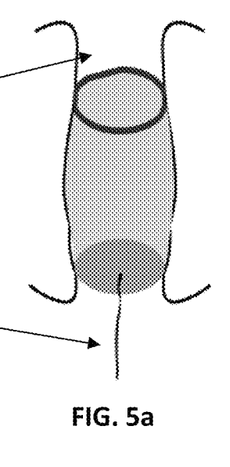
FIG. 5a: Fully distended Multipurpose Vaginal Occlusion and Distension Device which is tightly got fit inside the vaginal canal.

FIG. 5 shows the squeezed Multipurpose Vaginal Occlusion and Distension Device inserted into the vaginal canal wherein FIG. 5(*a*) shows the fully distended device which is tightly got fit inside the vaginal canal that will not get slipped off from the position where it is placed.

Figure 6:
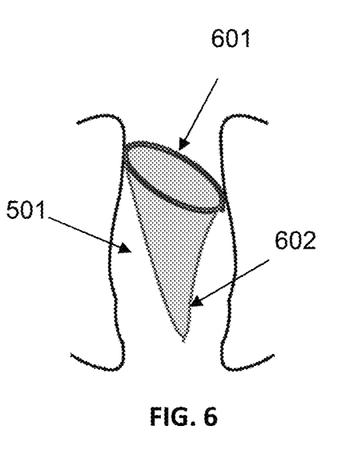
FIG. 6: Example of a conical shaped Menstrual cup positioned inside the vaginal canals, according to prior art.
Figure 41:
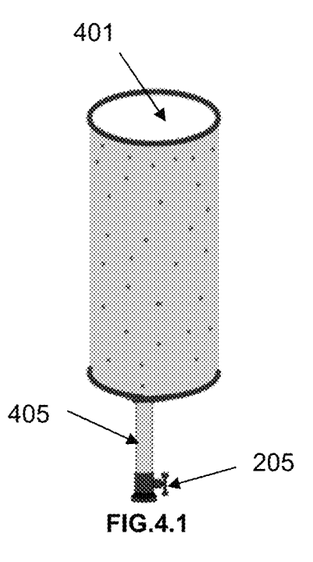

It can be seen from the FIG. 6, how the prior art shows one of the vaginal cup which is presently used with a conical shape is getting slipped off from the vaginal cavity where it is placed due to its shape of construction and instability.

1. Procedure for Using the Device in the Female Stress Urinary Incontinence and Fecal Incontinence:

The squeezable and inflatable Multipurpose Vaginal Occlusion and Distension Device with the closed anterior and posterior walls with the Distention Control and release Mechanism connected at the posterior wall as shown in FIG. 1 or FIG. 1*a* is squeezed and inserted into the vaginal cavity. With the Distention Control and release Mechanism (FIG. 2), the device can be inflated as per the convenience and comfort of the patient by herself. By inflating the device, the internal cavity of the device gets filled in with gas and that helps in getting proper distension and gets fit inside the vaginal canal so that it will not get slipped off as shown in (FIG. 5*a*). The provisions to inflate the tubular ribs and also the annular space according to an embodiment under the invention, helps in getting more controlled pressure and comfort of fit, while positioned inside the vaginal cavity, giving uniform pressure to the intrinsic sphincter muscles and hence helps to control stress urinary incontinence. Hence from the Multipurpose Vaginal Occlusion and Distension Device available in different sizes, having a wall thickness for the cylinder ranging from 0.5 mm to 4 mm with a diameter of 1 cm to 8 cm and a length of 2 cm to 8 cm, patients can choose as per their required size of comfort. Once the Multipurpose Vaginal Occlusion and Distension Device is properly inflated and placed inside the vaginal canal, the detachable Distention Control and release Mechanism (FIG. 2) can be removed. Similarly, whenever the patient wants, the Distention Control and release Mechanism (FIG. 2) can be reconnected for deflating the device before taking out.

2. Procedure for Using the Device as the Multipurpose Vaginal Occlusion and Distension Device for Collecting Menstrual Blood as an Alternative to Vaginal Cups and Pads:

The squeezable and inflatable Multipurpose Vaginal Occlusion and Distension Device with a fully opened anterior wall with a circular mouth of same inner diameter both at the anterior end and at the posterior end with single smooth layer on the cylindrical wall. The posterior wall having the gas inflow inlet is connected to the detachable Distention Control and release Mechanism (FIG. 2) is shown in FIG. 3. But Multipurpose Vaginal Occlusion and Distension Device shown in FIG. 3a is having double walled layer with corrugated outer layer. Whereas Multipurpose Vaginal Occlusion and Distension Device attached with "Distension control and release mechanism" having the corrugated outer layer with inflatable tubular rib spirally wound around the cylinder with the inflatable annular space, inflatable tubular ribs both at the anterior and posterior edges and or through the body of the device is shown in FIG. 3b. The cylindrical body of the device is squeezed well with hand and inserted into the vaginal cavity through the vaginal orifice. Depending on the device selected out of the one selected from FIG. 3, FIG. 3a, and FIG. 3b, the device can be inflated as per the convenience and comfort of the patient by herself. By inflating the device, the internal cavity of the device can be opened well for collecting the menstrual blood, as well as to get proper distension to fit inside the vaginal canal so that it will not get slipped off as shown in (FIG. 5a). The provisions to inflate the tubular ribs and also the annular space using the Distension Control and release Mechanism helps to get more controlled pressure and comfort of fit while placed inside the vaginal cavity. Hence the Multipurpose Vaginal Occlusion and Distension Devices are available in different size, having a wall thickness for the cylinder ranging from 0.5 mm to 4 mm with a diameter of 1 cm to 8 cm and a length of 2 cm to 8 cm. Ladies can choose the device as per their required size and of comfort. Once the Multipurpose Vaginal Occlusion and Distension Device is properly inflated and placed inside the vaginal canal, the detachable Distension Control and release Mechanism (FIG. 2) can be removed and similarly whenever the patient wants to take out the device, the Distension Control and release Mechanism (FIG. 2) can be reconnected and deflate the device to take out.

Figure 3C:
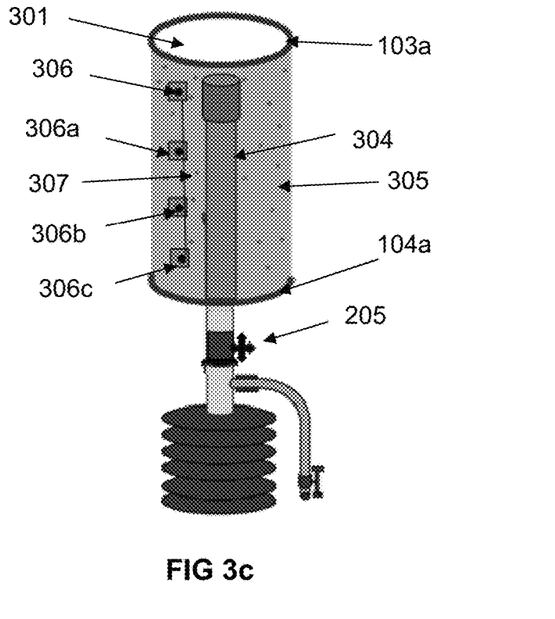
FIG. 3c: Transparent view of multipurpose Vaginal Occlusion and Distension Device attached with "Distension control and release mechanism" in which the gas inflow inlet is made to extended inside the cylindrical cavity of the device and the sensor chip embedded at the blood level marker at the internal space of the device while collecting Menstrual Blood, according to an embodiment under the invention.

According to a preferred embodiment under the invention, the multipurpose Vaginal Occlusion and Distension Device attached with "Distension control and release mechanism" explained above was modified to have additional features as shown in FIG. 3c. Here the gas inflow inlet (304) is extended inside the cylindrical cavity of the device, the height of which will be 0.5 cm below the mouth opening (301) and the sensor chips (306, 306a,306b,306c) are embedded at the blood level marker (307) at the internal space of the device for collecting Menstrual Blood.

In the event, if the device is filled with more blood than the desired level, the sensor chip embedded at the blood level marking (307), based on its settings, will give indicator alarm by the application which can be programmed to the users wrist watch or mobile phone and also the censer chips embedded at different level inside the device sense and measure the quantity of blood collected during every usage of the device.

3. Procedure to Use the Device as Multipurpose Vaginal Occlusion and Distension Device for Laparoscopic Surgeries.

The squeezable and inflatable Multipurpose Vaginal Occlusion and Distension Device with a full mouth opening having its diameter equal to that of the device or partly opened circular mouth or with circular multiple openings on the anterior wall with the posterior wall having gas inflow inlet and outflow tube connected with Coupling port with gas releasing and locking valve (205) that can be attached to Distension Control and release Mechanism is used for Laparoscopic Surgeries is shown in FIG. FIG. 4.1, FIG. 4.2, and FIG. 4.3. Whereas FIG. 4. shows the device attached with 'Distention Control and release Mechanism". Once the 'Distention Control and release Mechanism" is attached the tubular ribs and or the annular space can be inflated to make it fit inside the vaginal canal, if needed. Normally during laparoscopic surgeries, the CO2 gas already available inside the abdomen will help to fill up the device while doing the colpotomy (incising the vaginal vault) and further vaginal vault suturing is done in most cases. If the inflating and distension is insufficient, CO2 gas can be connected to the Gas inflow and outflow tube (203) of the "Distension control and release mechanism" and CO2 can be fed to the cylindrical space through the Gas flow tube Gas flow tube (405) available at the posterior end and connected with Coupling port (205) with gas releasing and locking valve. This functions as retractor means as well, once the "Distension control and release mechanism" is detached. In other words, the internal cavity of the device can also be filled up with the CO2 externally during colpotomy and vaginal vault suturing even by using the distension control and release mechanism connected through gas pipe line provided at the posterior end of the device, if the device is not properly filled up during colpotomy and vaginal vault suturing. Once the device is inserted and filled in with the gas, the device will take shape of the vaginal canal and will not get slipped off and can act as vaginal blocker and pneumoseal. Once the use of the device is over in laparoscopic procedure, the device can be deflated, squeezed and taken out from the vaginal cavity.

According to another embodiment under the invention, in its simpler version, the squeezable and inflatable Multipurpose Vaginal Occlusion and Distension Device with a full mouth opening having its diameter equal to that of the device or partly opened circular mouth or with circular multiple openings on the anterior wall, the posterior wall is closed and provided with flexible silicon thread (404) which functions as retractor means for removing the device from vaginal cavity as shown in FIG. 4.1a, FIG. 4.2a, and FIG. 4.3a. Any of these devices can be used by the surgeon by squeezing it and inserting into the vaginal cavity, based on the requirement.

I have brought out the novel features of the invention by explaining some of the preferred embodiments under the invention, enabling a person in the art to understand and visualize our invention. It is also to be understood that the invention is not limited in its application to the details set forth in the above description or illustrated in the drawings. Although the invention has been described in considerable detail with reference to certain preferred embodiments thereof, various modifications can be made without departing from the spirit and scope of the invention as described herein above and as defined in the following Claims.

I claim:
1. A Multipurpose vaginal occlusion and distension device with a distension controller comprises of:
   a cylindrical body having a uniform diameter ranging from 1 cm to 8 cm and a length ranging from 2 cm to 8 cm, made of a double layer polymeric membrane having a thickness of 0.5 to 4 mm with both anterior wall and posterior wall closed with similar double layered membrane making,
   an annular space between said two layers and cylindrical hollow internal space, which are inflatable, and both anterior and posterior circular edges of the said cylindrical body having respective anterior and posterior tubular silicon ribs (103a, 104a), each of said respective anterior and posterior tubular silicon ribs being separately independent of each other and formed by semi flexible metallic ring engulfed inside the silicon ribs which are also inflatable; and wherein the cylindrical body, upon being inflated, is positioned along a length of a vaginal canal such that the anterior and posterior circular edges of the cylindrical body, on being inflated, tightly fit along an inner circumference of the vaginal canal, wherein the posterior end is provided with a tubular opening having a gas flow tube connected with a coupling port with gas release and locking valve; wherein the coupling port with gas release and locking valve is connected to a connector port of a Distension control and release mechanism; wherein the Distension control and release mechanism is having a gas pumping bellows chamber, and a gas inflow and outflow tube provided with a gas inlet/out valve that is connected to an outlet of the gas pumping bellows chamber each of the gas inlet/outlet valve and the gas inflow and outlet tube to simultaneously inflate a cavity of the cylindrical body, the flexible annular space, the flexible tubular rib at the anterior circular edge and at the posterior circular edge, wherein the Distension control and release mechanism allows controlled pressure while placed inside the vaginal cavity giving uniform pressure to intrinsic sphincter muscles so as to control stress urinary incontinence such that when the device is inserted and filled in with the gas, the device takes shape of the vaginal canal and does not get slipped off and acts as a vaginal blocker and pneumoseal;

wherein the cylindrical body is reinforced by a tubular spiral rib (105) spirally wound around the cylindrical body which is inflatable, made of silicon with or without metallic soft spring thread engulfed by silicon, and connected to the tubular ribs at the anterior circular edges and at the posterior circular edges, so that the air pumping bellows chamber of the Distension control and release mechanism simultaneously inflates them, wherein when the cylindrical body is inserted inside the vaginal cavity, it comfortably fits inside the vaginal canal as per the choice of a user so as to prevent stress urinary incontinence and for fecal incontinence, and wherein the tubular spiral rib (105), which is wound spirally over the cylindrical part, is connectable to the tubular silicon ribs at the anterior side as well as at the posterior of the cylindrical part.

2. The Multipurpose vaginal occlusion and distension device as claimed in claim 1, wherein the outer layer of the cylindrical body is corrugated so that it helps to make the cylindrical body part comfortably fit inside the vaginal canal as per the choice of a user.

3. The Multipurpose vaginal occlusion and distension device as claimed in claim 1, the Distension control and release mechanism having the gas pumping bellows chamber by means of a Coupling port with the gas releasing and locking valve, and the outlet of the gas pumping bellows chamber is connected to the gas inflow and outflow tube provided with the gas inlet/outlet valves, having multiple channels to inflate which fills the flexible annular space formed by the double layered polymeric membranes, flexible tubular ribs at the anterior circular edge and at the posterior circular edge, the tubular rib spirally wound around the cylindrical body, and the cylindrical cavity.

* * * * *